(12) United States Patent
Chan et al.

(10) Patent No.: US 6,210,608 B1
(45) Date of Patent: Apr. 3, 2001

(54) NAPHTHOPYRANS AND PHENANTHROPYRANS ANNELATED IN $C_5$-$C_6$ WITH A BICYCLE GROUP AND COMPOSITIONS AND (CO) POLYMER MATRICES CONTAINING THEM

(75) Inventors: You-Ping Chan; Patrick Jean, both of Lyons (FR)

(73) Assignee: Corning S.A., Avon Cedex (FR)

( * ) Notice: Subject to any disclaimer, the term of this patent is extended or adjusted under 35 U.S.C. 154(b) by 0 days.

(21) Appl. No.: 09/504,689

(22) Filed: Feb. 16, 2000

(30) Foreign Application Priority Data

Feb. 17, 1999 (FR) .................................. 99 01914

(51) Int. Cl.$^7$ .......................... G02B 5/23; C07D 311/78; G02C 7/10
(52) U.S. Cl. .......................... 252/586; 549/331; 549/381; 549/382; 549/58; 549/60; 546/282.7; 546/98; 351/163
(58) Field of Search .......................... 252/286; 549/331, 549/381, 382, 58, 60; 546/282.7, 98; 351/163; 523/135

(56) References Cited

U.S. PATENT DOCUMENTS

| | | | |
|---|---|---|---|
| 3,567,605 | 3/1971 | Becker | 204/158 |
| 3,627,690 | 12/1971 | Casella et al. | 252/300 |
| 4,826,977 | 5/1989 | Heller et al. | 544/70 |
| 5,200,116 | 4/1993 | Heller | 252/586 |
| 5,238,981 | 8/1993 | Knowles | 524/110 |
| 5,411,679 | 5/1995 | Kumar | 252/586 |
| 5,429,744 | 7/1995 | Hagqvist | 210/493 |
| 5,451,344 | 9/1995 | Knowles et al. | 252/586 |
| 5,458,814 | 10/1995 | Kumar et al. | 252/586 |
| 5,645,767 | 7/1997 | Van gemert | 252/586 |
| 5,651,923 | 7/1997 | Kumar et al. | 252/586 |
| 5,698,141 | 12/1997 | Kumar et al. | 252/586 |
| 5,783,116 * | 7/1998 | Lin | 252/586 |

FOREIGN PATENT DOCUMENTS

| | | | |
|---|---|---|---|
| 95/05382 | 2/1995 | (WO) | C07D/491/04 |
| 95/27716 | 10/1995 | (WO) | C07D/498/04 |
| 96/14596 | 5/1996 | (WO) | G02B/5/23 |
| 97/21698 | 6/1997 | (WO) | C07D/311/78 |

* cited by examiner

Primary Examiner—Philip Tucker
(74) Attorney, Agent, or Firm—Angela N. Nwaneri; Peter Rogalskj

(57) ABSTRACT

The invention relates to novel naphthopyran- and phenanthropyran-type compounds having a carbobicycle annelated in 5,6-position. These compounds have formula (I) given below:

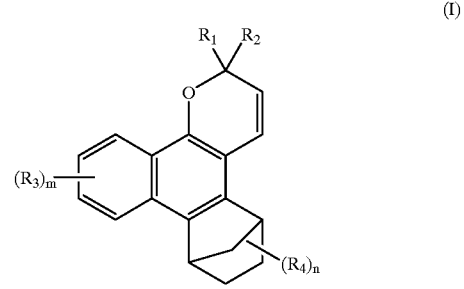

These compounds (I) have interesting photochromic properties. The invention also relates to their preparation, to their applications as photochromes, as well as to the compositions and (co)polymer matrices containing them.

33 Claims, No Drawings

NAPHTHOPYRANS AND PHENANTHROPYRANS ANNELATED IN $C_5$-$C_6$ WITH A BICYCLE GROUP AND COMPOSITIONS AND (CO) POLYMER MATRICES CONTAINING THEM

The present invention relates to novel annelated naphthopyran- or phenanthropyran-type compounds which have, in particular, photochromic properties. The invention also relates to photochromic compositions and photochromic ophthalmic articles (lenses for example) which contain said naphthopyrans or phenanthropyrans. The invention also covers the preparation of these novel compounds.

The photochromic compounds are capable of changing colour under the influence of a poly- or mono-chromatic light (UV for example) and of returning to their initial colour when the luminous irradiation ceases, or under the influence of temperature and/or a poly- or mono-chromatic light different from the first.

The photochromic compounds find applications in various fields, e. g. for the manufacture of ophthalmic lenses, contact lenses, solar protection glasses, filters, camera optics or photographic apparatus optics or other optical devices and observation devices, glazing, decorative objects, bill elements or even for information storage by optical inscription (coding).

In the field of ophthalmic optics, and in particular the spectacles trade, a photochromic lens which comprises one or more photochromic compounds must have:

a high transmission in the absence of ultraviolets, a low transmission (high colourability) under solar irradiation, adapted coloration and discoloration kinetics, a tint acceptable to the consumer (grey or brown preferably) with preferably a maintenance of the chosen tint during the coloration and the discoloration of the lens, a maintenance of the performances, the properties, within a temperature range of 0–40° C., a significant durability, since these objectives sought after are sophisticated corrective lenses and therefore expensive.

These lens characteristics are in fact determined by the active photochromic compounds which they contain; compounds which must furthermore be perfectly compatible with the organic or inorganic support which constitutes the lens.

Moreover, it is to be noted that obtaining a grey or brown tint may necessitate the use of at least two photochromes of different colours, i. e. having distinct maximal absorption wavelengths in the visible. This combination further imposes other requirements of the photochromic compounds. In particular, the coloration and discoloration kinetics of the (two or more) combined active photochromic compounds must be essentially identical. The same applies for their stability with time and also for their compatibility with a plastic or inorganic support.

Amongst the numerous photochromic compounds described in the prior art, benzopyrans and naphthopyrans may be cited which are described in patents or patent applications U.S. Pat. No. 3,567,605, U.S. Pat. No. 3,627,690, U.S. Pat. No. 4,826,977, U.S. Pat. No. 5,200,116, U.S. Pat. No. 5,238,981, U.S. Pat. No. 5,411,679, U.S. Pat. No. 5,429,744, U.S. Pat. No. 5,451,344, U.S. Pat. No. 5,458,814, U.S. Pat. No. 5,651,923, U.S. Pat. No. 5,645,767, U.S. Pat. No. 5,698,141, U.S. Pat. No. 5,783,116, WO-A-95 05382, FR-A-2,718,447, WO-A-96 14596, WO-A-97 21698 which are of the reduced formulae below:

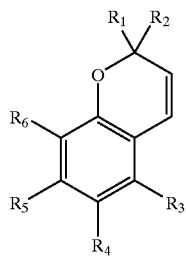 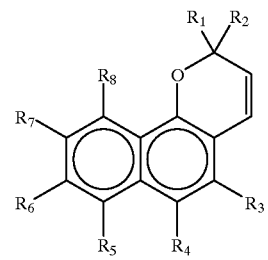

Benzopyrans  Naphthopyrans

The U.S. Pat. No. 5,651,923 patent notably claims the general structure below:

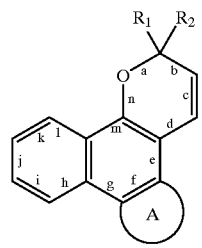

U.S. Pat. No. 5,651,923 in which ring A, annelated with side $f$, is a benzothieno-, benzofurano- or indolo-type heterocycle.

The U.S. Pat. No. 5,783,116 patent describes more specifically naphthopyrans of the following general structure

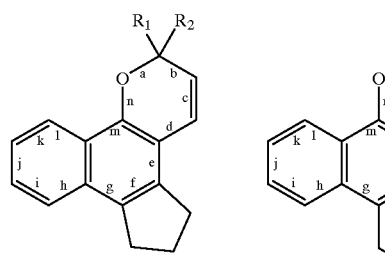

These compounds claim to satisfy the specifications defined above. In reality, if these compounds really do have one or more of the basic properties sought after, such as a high transmission in the absence of ultraviolets and a high colourability under solar irradiation, none of the compounds described hitherto have the complete combination of the properties sought after which are necessary for the production of satisfactory articles. In particular, none of these compounds is intrinsically grey or brown and the necessity of using an additional photochrome in order to obtain one of these two tints does subsist.

In this context, it is to the credit of the inventors for having been interested in this type of derivative as a base for developing novel photochromes, and for having proposed a novel family of molecules which have particularly advantageous photochromic properties.

Thus, according to a first of its aspects, the present invention relates to compounds of formula (I):

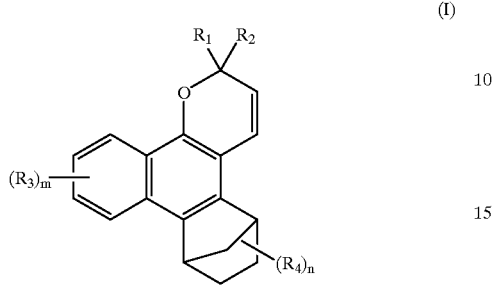

in which:
$R_1$ and $R_2$, which are identical or different, represent, independently:
hydrogen,
a linear or branched alkyl group comprising 1 to 12 carbon atoms,
a cycloalkyl group comprising 3 to 12 carbon atoms,
an aryl or heteroaryl group comprising in its basic structure 6 to 24 carbon atoms or 4 to 24 carbon atoms respectively and at least one heteroatom selected from sulphur, oxygen and nitrogen; said basic structure being optionally substituted with at least one substituent selected from the whole of the substituents given below:
a halogen, and notably fluorine, chlorine and bromine,
a linear or branched alkyl group comprising 1 to 12 carbon atoms,
a linear or branched alkoxy group comprising 1 to 12 carbon atoms,
a haloalkyl or haloalkoxy group corresponding to the ($C_1$–$C_{12}$) alkyl or alkoxy groups above respectively which are substituted with at least one halogen atom, and notably a fluoroalkyl group of this type,
a linear or branched alkenyl group comprising 2 to 12 carbon atoms, and notably a vinyl group or an allyl group,
an —$NH_2$ group,
an —NHR group, R representing a linear or branched alkyl group comprising 1 to 6 carbon atoms,
a

group, R' and R", which are identical or different, representing independently a linear or branched alkyl group comprising 1 to 6 carbon atoms or representing together with the nitrogen atom to which they are bound a 5- or 7-membered ring which can comprise at least one other heteroatom selected from oxygen, sulphur and nitrogen, said nitrogen being optionally substituted with an R'" group, which is a linear or branched alkyl group comprising 1 to 6 carbon atoms, a methacryloyl group or an acryloyl group,
an aralkyl or heteroaralkyl group, the alkyl group, which is linear or branched, comprising 1 to 4 carbon atoms and the aryl part of which has the same definition as that given supra for the aryl and heteroaryl group; or
said two substituents $R_1$ and $R_2$ together form an adamantyl, norbornyl, fluorenylidene, di($C_1$–$C_6$) alkylanthracenylidene or spiro($C_5$–$C_6$) cycloalkylanthracenylidene group; said group being optionally substituted with at least one of the substituents listed above for $R_1$, $R_2$: an aryl or heteroaryl group;
$R_3$, which are identical or different, represent, independently:
a halogen, and notably fluorine, chlorine or bromine,
a linear or branched alkyl group comprising 1 to 12 carbon atoms (advantageously 1 to 6 carbon atoms),
a cycloalkyl group comprising 3 to 12 carbon atoms,
a linear or branched alkoxy group comprising 1 to 12 carbon atoms (advantageously 1 to 6 carbon atoms),
a haloalkyl, halocycloalkyl, or haloalkoxy group corresponding to the alkyl, cycloalkyl, alkoxy groups above respectively, which are substituted with at least one halogen atom, notably selected from fluorine, chlorine and bromine,
an aryl or heteroaryl group having the same definition as that given supra for $R_1$, $R_2$,
an aralkyl or heteroaralkyl group, the alkyl group, which is linear or branched, comprising 1 to 4 carbon atoms, and the aryl and heteroaryl groups having the same definitions as those given supra for $R_1$, $R_2$,
an amine or amide group: —$NH_2$, —NHR, —$CONH_2$,—CONHR,

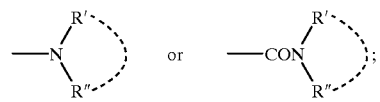

R, R', R" having their respective definitions given supra for the amine substituents of the values $R_1$, $R_2$: aryl or heteroaryl,
an —$OCOR_6$ or —$COOR_6$ group, $R_6$ representing a straight or branched alkyl group comprising 1 to 6 carbon atoms, or a cycloalkyl group comprising 3 to 6 carbon atoms, or a phenyl group, optionally substituted with at least one of the substituents listed above for the values of $R_1$, $R_2$: aryl or heteroaryl or
at least two of the $R_3$ groups, which are adjacent, form a 5- to 6-membered aromatic or non-aromatic ring which can comprise at least one heteroatom selected from the group comprising: oxygen, sulphur or nitrogen and/or at least one substituent selected from a $C_1$–$C_6$ alkyl group which is linear or branched, a $C_1$–$C_6$ alkoxy group which is linear or branched, and an amine g of formula —$NH_2$, —NHR or

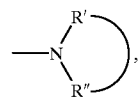

as defined above, as substituent, of the basic structure of the aryl or heteroaryl group representing $R_1$ or $R_2$;
m is an integer of 0 to 4

$R_4$, which are identical or different, represent, independently:

a halogen, preferably selected from the group comprising fluorine, chlorine and bromine, or a $C_1$–$C_6$ alkyl group which is linear or branched;

n is an integer of 0 to 4.

The person skilled in the art will obviously have understood that the branched alkyl, alkoxy and alkenyl groups, as defined above, comprise a sufficient number of carbon in order to be branched (i.e. more than 3, more than 3, and more than 4 carbon atoms respectively).

The compounds of the invention—naphthopyrans or phenanthropyrans of formula (I)—have a high colourability, even at 40° C., combined with discoloration kinetics which are adapted to the applications sought after. The colours, which may be attained easily, vary from orange to blue.

Amongst said compounds of the invention, preferred are those which have the formula (I) in which:

$R_1$, $R_2$ are identical or different and represent independently optionally substituted aryl or heteroaryl groups the basic structure of which is selected from the group comprising phenyl, naphthyl, biphenyl, pyridyl, furyl, benzofuryl, dibenzofuryl, N—($C_1$–$C_6$)alkylcarbazole, thienyl, benzothienyl, dibenzothienyl and julolidinyl groups; $R_1$ and/or $R_2$ representing, advantageously, a para-substituted phenyl group; or $R_1$ and $R_2$ together form an adamantyl or norbornyl group.

According to a first embodiment of the invention, the compounds (I) are such that at least two of their adjacent $R_3$ substituents do not together form a ring.

According to a second embodiment of the invention, the compounds (I) are such that they comprise at least two adjacent $R_3$ groups which together form an annelated carbocycle or heterocycle, which is optionally substituted (with a $C_1$–$C_6$ alkyl or alkoxy group, or with an amine group).

According to a variant of this second embodiment, the invention relates to the following phenanthrene structures of formulae (I.1) and (I.2):

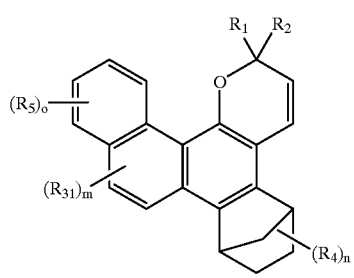

(I.1)

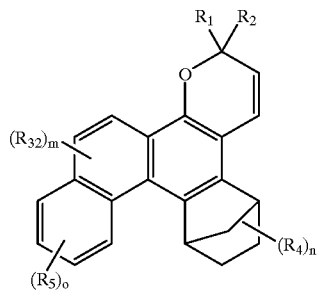

(I.2)

in which $R_1$, $R_2$ and $R_4$ are as defined above; $R_{31}$ and $R_{32}$ represent, independently, a group having the same definition as that given supra for $R_3$ in the generic formula (I) which includes the two embodiments described above; $R_5$ represents an alkyl, alkoxy or amine group as defined above, and m=0, 1, 2, n=0 to 4 and o=0 to 4.

In accordance with an interesting provision of the invention, notably in accordance with the two above-mentioned embodiments proper, n=0 in formulae (I), (I.1) or (I.2).

According to a second of its aspects, the present invention relates to a method of preparing the compounds (I), characterised in that it essentially consists in carrying out a condensation:

of at least one of the intermediate products of formulae (II.1), (II.2), (II.3) given below:

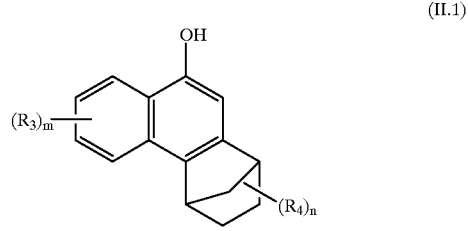

(II.1)

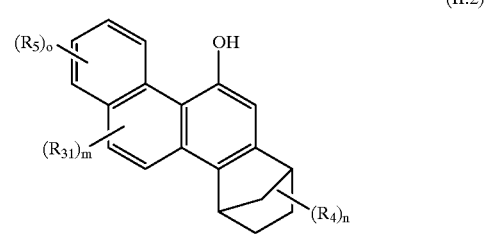

(II.2)

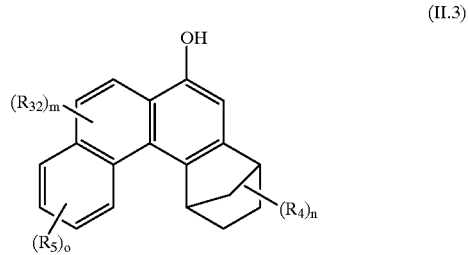

(II.3)

in which $R_3$, $R_{31}$, $R_{32}$, $R_4$, $R_5$, m, n and o are as defined above with reference to formulae (I), (I.1), (I.2);

with at least one derivative of propargylic alcohol having formula (III) below:

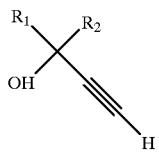

(III)

in which $R_1$ and $R_2$ are as defined supra with reference to formula (I);

the condensation (II)/(III) being carried out advantageously in the presence of a catalyst, this catalyst being preferably selected from the group comprising para-toluenesulphonic acid, dodecylsulphonic acid or bromoacetic acid; or with at least one aldehyde derivative, having formula (III') below:

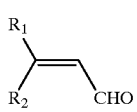

(III')

in which $R_1$ and $R_2$ are as defined supra with reference to formula (I);

the condensation (II)/(III') being carried out, advantageously, in the presence of a metallic complex, preferably a complex of titanium, titanium (IV) ethoxide being particularly preferred.

In practice, the condensation reaction between compounds (II) and (III') can take place in solvents such as toluene, xylene or tetrahydrofuran, to which appropriate catalysts are optionally added. For more details on the condensation of compounds (II), (III'), reference may be made to the EP-A-0 562 915 patent application.

The compounds of formula (III) are known to the person skilled in the art and are obtained from the corresponding ketone according to a method described notably in the WO-A-96 14596 patent application. The ketone is itself commercial or is prepared according to the known methods such as the Friedel Crafts method (cf. WO-A-96 14596 and cited references).

Aldehydes (III'), which are derivatives of (III), are obtained by rearrangement in an acid medium (cf. *J. Org Chem.*, 1977, 42, 3403).

The compounds of formula (II) are obtained according to a synthetic scheme the various steps of which are adaptations of known methods. The preferred general synthetic schemes are given below, for compound (II.1). The compounds of formula (II.2) and (II.3) can be obtained by the same routes starting from the organomagnesium reagent of 2-bromo- or 1-bromonaphthalene respectively.

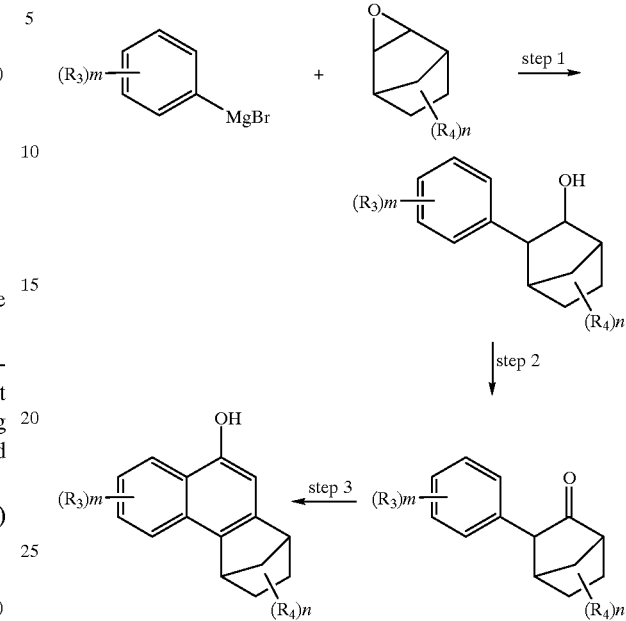

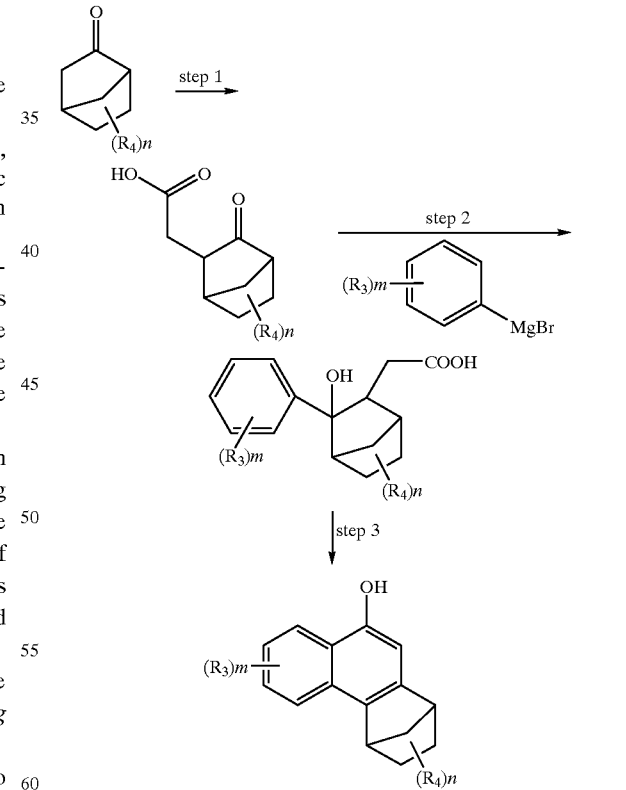

Concerning route A, step 1 is carried out according to a method described by Basavaiaiah et al. (Tetraliedron Asymm. 1994, 5, 223–234), step 2 by Corey et al. (Tetrahedron Lett. 1975, 2647) and step 3 by Sepiol et al. (Synthesis 1979, 290). Concerning route B, step 1 is carried out according to a method described by Schoenleber et al. (WO-A-96 38435) and steps 2 and 3 according to Lin (U.S. Pat. No. 5,783,116).

According to a third of its aspects, the invention also relates to the novel intermediate products of formulae (II.1), (II.2), (II.3) recalled below:

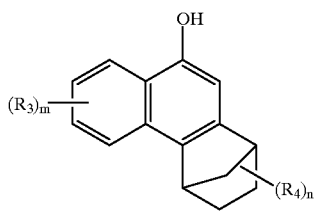

(II.1)

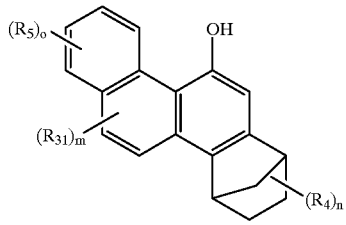

(II.2)

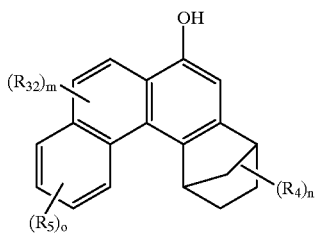

(II.3)

in which $R_3$, $R_{31}$, $R_{32}$, $R_4$, $R_5$, m, n and o are as defined supra with reference to formulae (I), (I.1) and (I.2).

The naphthopyrans or phenanthropyrans of the invention are obtained by the condensation of at least one compound having a formula type (II) (with a compound of formula III or III').

According to a fourth of its aspects, the object of the invention is (co)polymer(s) and/or reticulate(s) obtained by polymerising and/or cross-linking at least one monomer consisting of a compound (I) as defined above. Thus, the compounds (I) according to the invention can be per se (co)monomers and/or be comprised in (co)polymerisable and/or cross-linkable (co)monomers. The (co)polymers and/or reticulates thus obtained can constitute photochromic matrices such as those presented infra.

According to a fifth of its aspects, the present invention relates to the use of said compounds of formula (I) of the invention as photochromic agents. Another object of the invention is, therefore:

firstly, novel photochromic compounds which are constituted by the naphthopyran or phenanthropyran derivatives such as defined above, taken alone or in a mixture of themselves and/or with at least one other photochromic compound of another type and/or with at least one non-photochromic colouring agent;

secondly, novel photochromic compositions which comprise at least one compound (I) as defined above, and/or one of its derivatives, and/or at least one linear or cross-linked (co)polymer containing at least one compound (I) according to the invention in its structure. Such photochromic compositions can contain at least one other photochromic compound, of another type and/or at least one non-photochromic colouring agent and/or at least one stabilising agent. These photochromic compounds of another type, non-photochromic colouring agents, and stabilising agents are prior art products known to the person skilled in the art.

Within the context of the present invention, combinations of photochromic compounds of the invention and/or combinations of photochromic compounds of the invention and photochromic compounds of another type according to the prior art are particularly recommended; such combinations being interesting in that they are suitable for generating grey or brown tints, which are desired by the public in applications such as ophthalmic spectacles or solar spectacles. These additional photochromic compounds can be those known to the person skilled in the art and described in the literature, e. g. chromenes (U.S. Pat. No. 3,567,605, U.S. Pat. No. 5,238,981, WO-A-94 22850, EP-A-0 562 915), spiropyrans or naphthospiropyrans (U.S. Pat. No. 5,238, 981) and spiroxazines (Crano et al., "Applied Photochromic Polymer Systems", Ed. Blackie & Son Ltd, 1992, chapter 2).

Said compositions according to the invention can also comprise:

non-photochromic colouring agents which enable adjusting the tint, and/or one or more stabilising agents, such as an anti-oxidising agent for example, and/or one or more anti-UV, and/or one or more anti-radicals, and/or one or more photochimic excited state deactivators.

These additives can notably enable improving the durability of said compositions.

The compounds of the invention envisaged within the context of their photochromic applications can be used in solution. Thus, a photochromic solution can be obtained by dissolving at least one of said compounds in an organic solvent such as toluene, dichloromethane, tetrahydrofuran or ethanol. The solutions obtained are in general colourless and transparent. When exposed to sunlight, they develop a strong coloration and regain the colourless state when they are placed in an area of less exposure to the sun's rays or, in other words, when they are no longer submitted to UV. In general, a very low concentration of product (of the order of 0.01 to 5% by weight) is sufficient to obtain an intense coloration.

The compounds according to the invention are furthermore compatible with support matrices of organic polymer or of inorganic material, in a form included in said matrices as well as in the form of a coating of said matrices.

Also, within the context of the fourth aspect of the invention in relation to the photochromic applications, the object of the invention is a matrix which comprises:

at least one compound (I), as defined supra;

and/or at least one (co)polymer and/or reticulate, as defined supra;

and/or at least one composition, as presented above.

The most interesting applications of the compounds of the invention are in fact those in which the photochrome is dispersed uniformly within or on the surface of a matrix formed by a polymer and/or copolymer and/or mixture of (co)polymers.

Following the example of their behaviour in solution, the compounds (I), included in a polymer matrix are colourless or slightly coloured in the initial state and rapidly develop an intense coloration under a UV light (365 nm) or under a light source of the solar type. Finally, they regain their initial coloration once the irradiation ceases.

The methods of implementation which can be envisaged in order to obtain such a matrix are very varied. Amongst those known to the person skilled in the art, the diffusion in the (co)polymer, from a suspension or solution of the photochrome, in a silicone oil, in an aliphatic or aromatic hydrocarbon, or in a glycol, or from another polymer matrix, can be cited for example. The diffusion is commonly carried out at a temperature of 50 to 200° C. for a period of time of 15 minutes to several hours, according to the nature of the polymer matrix. Another implementation technique consists in mixing the photochrome in a formulation of polymerisable matrices, depositing this mixture on a surface or in a mould, and then carrying out the copolymerisation. These implementation techniques, and others, are described in the article by Crano et al. "Spiroxazines and their use in photochromic lenses" published in Applied Photochromic Polymer Systems, Ed. Blackie and Son Ltd—1992.

The following products may be mentioned as examples of preferred polymer materials for forming matrices which are useful in optical applications of the photochromic compounds according to the invention:

alkyl, cycloalkyl, (poly or oligo)ethylene glycol, aryl or arylalkyl mono-, di- tri- or tetraacrylate or mono-, di-, tri- or tetramethacrylate, which is optionally halogenated or which comprises at least one ether and/or ester and/or carbonate and/or carbamate and/or thiocarbamate and/or urea and/or amide group, polystyrene, polyether, polyester, polycarbonate (e.g. bisphenol-A polycarbonate, diallyl diethylene glycol polycarbonate), polycarbamate, polyepoxy, polyurea, polyurethane, polythiourethane, polysiloxane, polyacrylonitrile, polyamide, aliphatic or aromatic polyester, vinylic polymers, cellulose acetate, cellulose triacetate, cellulose acetate-propionate or polyvinylbutyral, those obtained from difunctional monomers having the formula below:

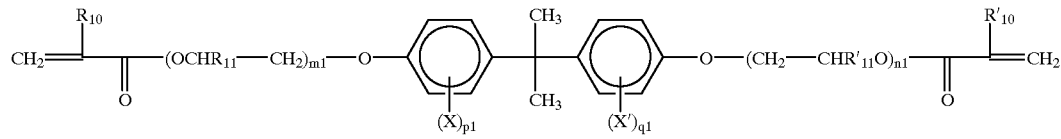

in which:

$R_{10}$, $R'_{10}$, $R_{11}$ and $R'_{11}$ are identical or different and represent independently a hydrogen or a methyl group;

$m_1$ and $n_1$ are, independently, integers between 0 and 4 (inclusive); and are advantageously independently equal to 1 or 2;

X and X', which are identical or different, are a halogen and represent, preferably, a chlorine and/or a bromine;

$p_1$ and $q_1$ are, independently, integers between 0 and 4 (inclusive);

copolymers of at least two types of copolymerisable monomers selected from the precursor monomers of the polymers listed supra, and preferably those belonging to the groups comprising: (meth)acrylic monomers, vinylic monomers, allylic monomers, and mixtures thereof.

In a particularly preferred manner, the photochromes of the invention are used with resins which have a nanobiphasic structure and which are obtained by copolymerising at least two different, specific difunctional monomers. Such resins have been described by the Applicant in the French patent Application FR-A-2,762,845.

The amount of photochrome used in the (co)polymer matrix depends upon the degree of darkening desired. Usually, between 0.001 and 20% by weight of it is used.

Still according to the fifth of its aspects in relation to the applications of the compounds (I) as photochromes, another object of the present invention is ophthalmic articles, such as ophthalmic or solar spectacle articles, comprising:

at least one compound (I) according to the invention, and/or at least one (co)polymer and/or reticulate formed, at least in part, from compound(s) of the invention, and/or at least one photochromic composition as defined above, and/or at least one matrix (as defined supra), of an organic polymer material or of an inorganic material, or even of a hybrid inorganic-organic material, said matrix initially optionally comprising at least one compound of the invention.

In practice, the articles which are more particularly covered by the present invention are ophthalmic lenses or photochromic solar lenses, glazing (windows for buildings, for locomotion engines, automobile vehicles), optical devices, decorative articles, solar protection articles, information storage, . . . .

The present invention is illustrated by the Examples which follow of synthesis and of photochromic validation, of compounds of the invention. Said compounds of the invention are compared to prior art compounds $C_1$, $C_2$ and $C_3$.

EXAMPLES

Example 1

Synthesis of Compound (1)

The synthesis of compound (1) was carried out according to route A described supra.

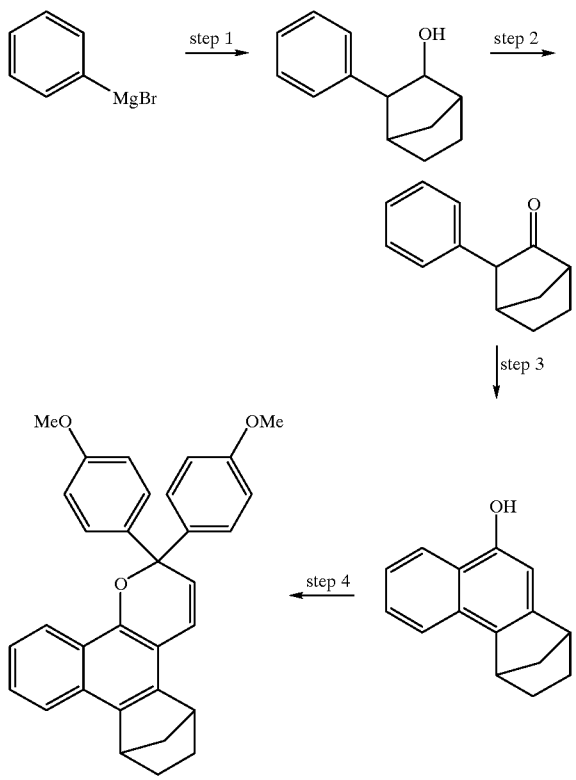

Step 1:

In a 250 ml conical flask, the following products are loaded in the order: 40 ml of THF, 33.5 ml of PhMgBr (3M ether) and 3.4 g of CuI. The mixture is cooled to −30° C., and a solution of 10 g of epoxynorbornane in 50 ml of THF is then poured in. After 30 minutes at −30° C., the temperature is allowed to rise to 25° C. and after 16 hours, the medium is poured into an ammonium chloride solution. The organic phase is recovered, washed with 3×150 ml of an ammonium chloride solution, and then dried over magnesium sulphate. 12.5 g of an oil are recovered which contains the desired product.

Step 2:

In a 500 ml conical flask, the following products are loaded in the order: 11.5 g of the product of the preceding step, 200 ml of dichloromethane, 60 g of Celite and 39 g of pyridinium chlorochromate. After 1.5 hours at ambient temperature, 200 ml diisopropyl ether are poured into the medium and the suspension is filtered. After evaporation to dryness, 12 g of a brown liquid are recovered that is purified by chromatography on silica in eluting with a toluene/dichloromethane 80/20 mixture. 5.84 g of the desired product are recovered in the form of an oil.

Step 3:

In a 250 ml conical flask equipped with a Dean-Stark collector, the following mixture: 5.85 g of the product of the preceding step, 3.55 g of ethyl cyanoacetate, 2.7 g of ammonium acetate, 2.2 g of acetic acid and 100 ml of toluene, is heated under reflux for 24 hours. 10 g of acetamide are then added and the toluene is distilled off. After 6 hours at 200–220° C., the medium is poured into 300 ml of water, and the product is then extracted with a THF/ethyl acetate mixture. The product is then purified by chromatography on silica in eluting with a toluene/dichloromethane 60/40 mixture. 1.37 g of the desired intermediate product are isolated after recrystallisation.

The following mixture 1.37 g of the product of the preceding step, 2.7 g of KOH in 15 ml of n-butanol, is heated at about 200–220° C. for 6 hours in a 125 ml acid digestion bomb. After cooling, the mixture is transferred into a flask and is then reduced to dryness. The paste is then dissolved in 50 ml of water and is then neutralised by the slow and progressive addition of concentrated hydrochloric acid. The product is extracted with 60 ml of diisopropyl ether, washed with 2×100 ml of water and then dried over magnesium sulphate. After evaporation to dryness, 1.3 g (98%) of a brown oil are recovered.

Step 4:

The following mixture: 0.5 g of the product of the preceding step, 0.78 g 1,1-bis(para-methoxyphenyl)propyne-1-ol in 10 ml of dichloromethane, is heated under reflux in the presence of a catalytic amount of bromoacetic acid in a 100 ml reactor for 5 hours. The product is then purified by chromatography on silica in eluting with toluene. The purest fractions are combined which are reduced to dryness. About 50 mg of the desired photochrome are obtained. Its structure is confirmed by NMR spectroscopy.

Example 2

Synthesis of Compound (2)

The synthesis of compound (2) was carried out according to route A described supra.

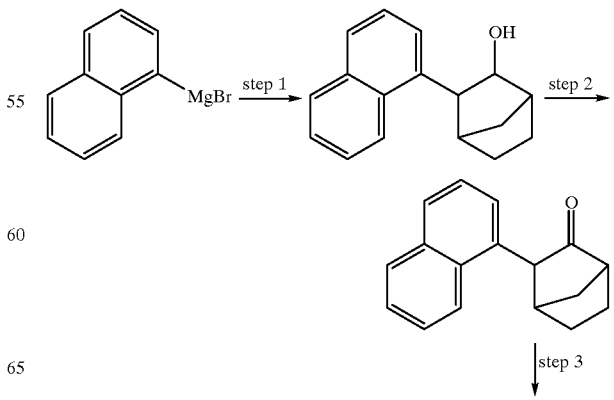

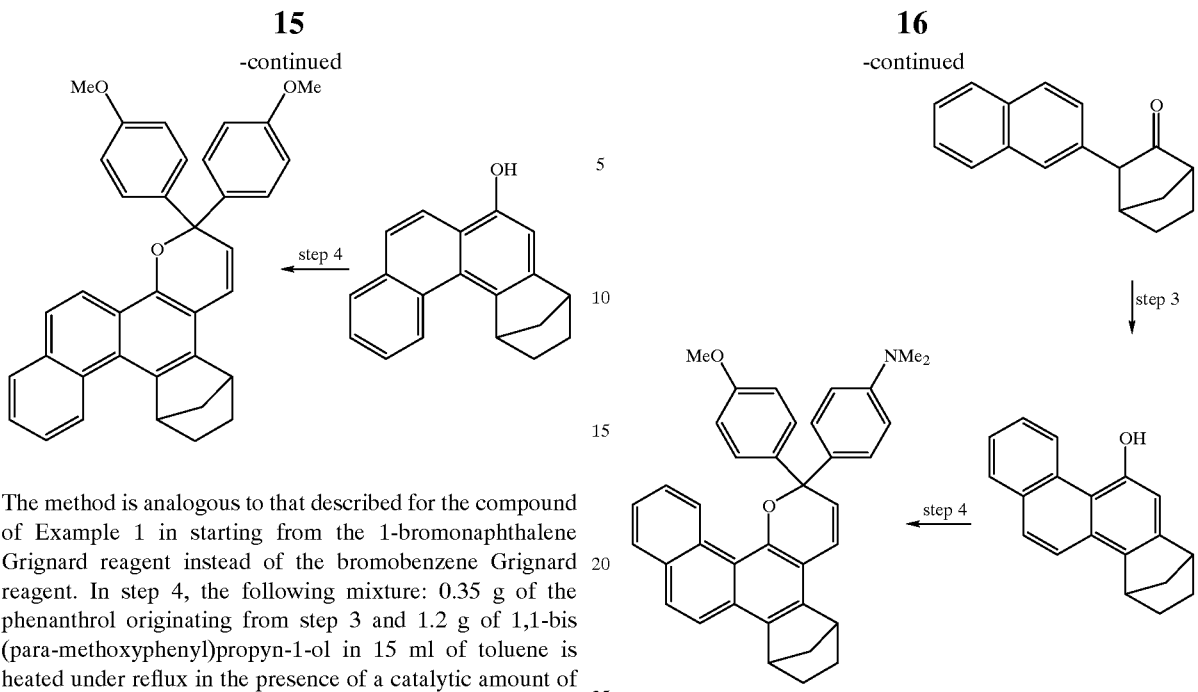

The method is analogous to that described for the compound of Example 1 in starting from the 1-bromonaphthalene Grignard reagent instead of the bromobenzene Grignard reagent. In step 4, the following mixture: 0.35 g of the phenanthrol originating from step 3 and 1.2 g of 1,1-bis (para-methoxyphenyl)propyn-1-ol in 15 ml of toluene is heated under reflux in the presence of a catalytic amount of bromoacetic acid for 4 hours. The product is then purified by chromatography on silica in eluting with a toluene/heptane 80/20 mixture. The purest fractions are combined and are reduced to dryness. A recrystallisation in a toluene/heptane mixture at 0° C. enables isolating about 50 mg of the desired photochrome. Its structure is confirmed by NMR spectroscopy.

Example 3

Synthesis of Compound (3)

The method is analogous to that described for the preceding product. In step 4, the following mixture: 0.35 g of the phenanthrol originating from step 3 and 1.2 g of 1-phenyl-1-(para-dimethylaminophenyl)-propyn-1-ol in 15 ml of toluene is heated under reflux in the presence of a catalytic amount of bromoacetic acid for 14 hours. The product is then purified by chromatography on silica in eluting with a toluene/heptane 80/20 mixture. The purest fractions are combined and are reduced to dryness. A recrystallisation in a toluene/heptane mixture at 0° C. enables isolating about 50 mg of the desired photochrome. Its structure is confirmed by NMR spectroscopy.

Example 4

Synthesis of Compound (4)

The synthesis of compound (4) was carried out according to route A described supra.

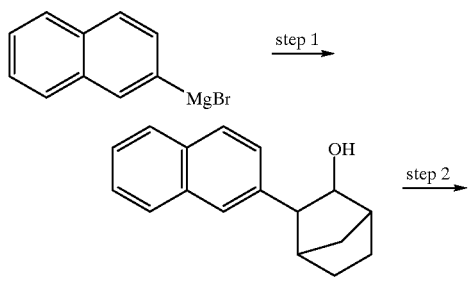

The method is analogous to that described for the compound of Example 1 in starting from the 2-bromonaphthalene Grignard reagent instead of the bromobenzene Grignard reagent. In step 4, the following mixture: 0.7 g of the phenanthrol originating from step 3 and 1.0 g of 1-(para-methoxyphenyl)-1-(para-dimethylaminophenyl)propyn-1-ol in 15 ml of toluene is heated under reflux in the presence of a catalytic amount of bromoacetic acid for 7 hours. The product is then purified by chromatography on silica in eluting with a toluene/heptane 70/30 mixture.

The purest fractions are combined and are reduced to dryness. A recrystallisation in a toluene/heptane mixture at 0° C. enables isolating about 140 mg of the desired photochrome. Its structure is confirmed by NMR spectroscopy.

Example 5

Compounds C1, C2 AND C3

Compound C1 is commercially available. Compounds C2 and C3 are described in the U.S. Pat. No. 5,783,116 patent.

Example 6

The photochromic properties of said compounds (1), (2), (3), (4), C1, C2 and C3 were evaluated.

Said compounds are dissolved, at the rate of 5 mg in 50 ml of THF. The UV-visible absorptions (optical path of 1 cm) are then measured before and after exposure to a 365 nm UV source. The observation of the tints and intensities developed is made by placing the solutions in the sun or before a solar simulator. The properties of these compounds are given in the Table below.

| COM-POUND | STRUCTURE | λ1* | λ2** |
|---|---|---|---|
| (1) | 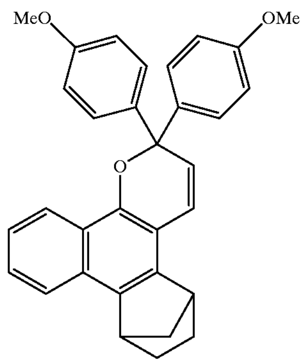 | 375 nm | 529 nm |
| (2) | 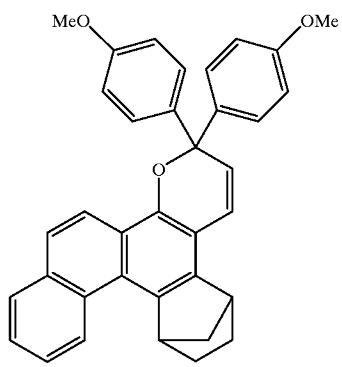 | 394 nm | 580 nm |
| (3) | 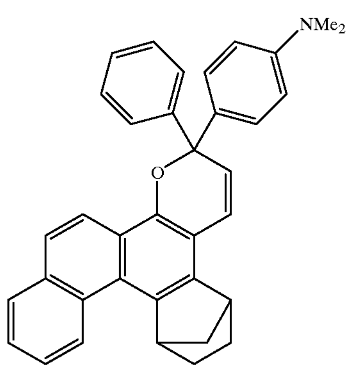 | 393 nm | 601 nm |
| (4) | 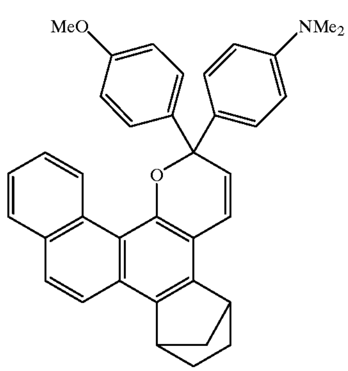 | 390 nm | 602 nm |

-continued

| COM-POUND | STRUCTURE | λ1* | λ2** |
|---|---|---|---|
| (C1) | 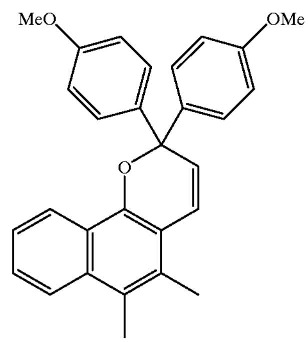 | 369 nm | 490 nm |
| (C2) | 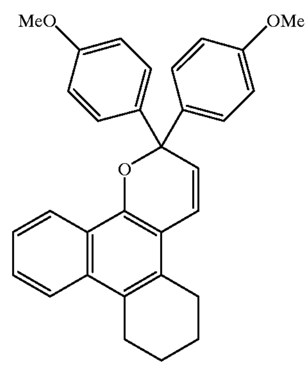 | 369 nm | 490 nm |
| (C3) | 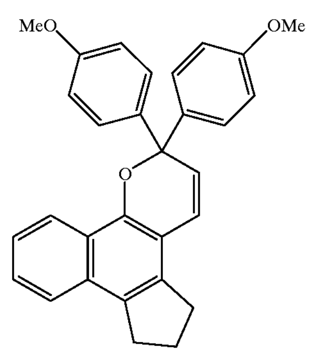 | 374 nm | 508 nm |

*λ1 max of the band of the longest wavelength of the compound before exposure.

**λ2 max of the band of the longest wavelength of the compound after exposure.

The observation of the solutions in the presence of solar or UV rays shows that the compounds of the invention have λ1 and λ2 which are shifted towards longer wavelengths (bathochromic shift). This observation is especially evident by comparing the λmax's of the compound (1) with the analogous compounds C1, C2 and C3.

What is claimed is:

1. A compound of the following formula

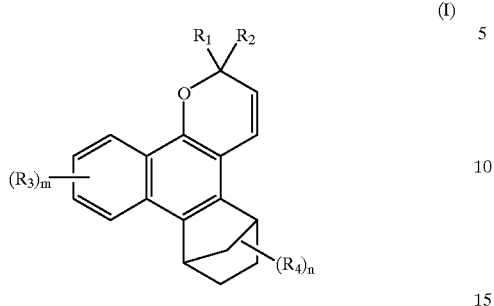

(I)

in which:

R₁ and R₂, which are identical or different, represent, independently:
hydrogen,
a linear or branched alkyl group comprising 1 to 12 carbon atoms,
a cycloalkyl group comprising 3 to 12 carbon atoms,
an aryl or heteroaryl group comprising, in its basic structure, 6 to 24 carbon atoms or 4 to 24 carbon atoms, respectively, and at least one heteroatom selected from sulphur, oxygen and nitrogen; said basic structure being optionally substituted with at least one substituent selected from the group consisting of:
a halogen,
a linear or branched alkyl group comprising 1 to 12 carbon atoms,
a linear or branched alkoxy group comprising 1 to 12 carbon atoms,
a haloalkyl or haloalkoxy group corresponding to the (C₁–C₁₂) alkyl or alkoxy groups above, respectively, which are substituted with at least one halogen atom,
a linear or branched alkenyl group comprising 2 to 12 carbon atoms,
an —NH₂ group,
an —NHR group, R representing a linear or branched alkyl group comprising 1 to 6 carbon atoms,
a

group, wherein R' and R", which are identical or different, represent independently a linear or branched alkyl group comprising 1 to 6 carbon atoms or represent together with the nitrogen atom to which they are bound a 5- or 7-membered ring which can comprise at least one other heteroatom selected from oxygen, sulphur, and nitrogen, said nitrogen being optionally substituted with an R'" group, which is a linear or branched alkyl group comprising 1 to 6 carbon atoms, and
a methacryloyl group or an acryloyl group,
an aralkyl or heteroaralkyl group, the alkyl part of which is linear or branched and comprises 1 to 4 carbon atoms and the aryl or heteroaryl part of which has the same definition as that given supra for the aryl and heteroaryl group; or
said two substituents R₁ and R₂ together form an adamantyl, norbornyl, fluorenylidene, di(C₁–C₆)alkylanthracenylidene, or spiro(C₅–C₆)cycloalkylanthracenylidene group; said group being optionally substituted with at least one substituent selected from the group consisting of:
a halogen,
a linear or branched alkyl group comprising 1 to 12 carbon atoms,
a linear or branched alkoxy group comprising 1 to 12 carbon atoms,
a haloalkyl or haloalkoxy group corresponding to the (C₁–C₁₂) alkyl or alkoxy groups above respectively which are substituted with at least one halogen atom,
a linear or branched alkenyl group comprising 2 to 12 carbon atoms,
an —NH₂ group,
an —NHR group, R representing a linear or branched alkyl group comprising 1 to 6 carbon atoms,
a

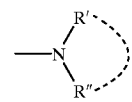

group in which R₁ and R" are identical or different and independently represent a linear or branched alkyl group comprising 1 to 6 carbon atoms, or R' and R", together with the nitrogen atom to which they are bound, represent a 5- or 7-membered ring which can comprise at least one other heteroatom selected from oxygen, sulphur, and nitrogen, said nitrogen being optionally substituted with an R'" group which is a linear or branched alkyl group comprising 1 to 6 carbon atoms, and
a methacryloyl group or an acryloyl group;

R₃, which are identical or different, represent, independently:
a halogen,
a linear or branched alkyl group comprising 1 to 12 carbon atoms,
a cycloalkyl group comprising 3 to 12 carbon atoms,
a linear or branched alkoxy group comprising 1 to 12 carbon atoms,
a haloalkyl, halocycloalkyl, or haloalkoxy group corresponding to the alkyl, cycloalkyl, or alkoxy groups above, respectively, which are substituted with at least one halogen atom,
an aryl or heterozryl group having the same definition as that given supra for R₁, R₂,
an aralkyl or heteroaralkyl group, the alkyl part of which is linear or branched and comprises 1 to 4 carbon atoms, and the aryl and heteroaryl part of which has the same definitions as those given supra for the aryl or heteroaryl groups for R₁, R₂,
an amine or amide group: —NH₂, —NHR, —CONH₂, —CONHR,

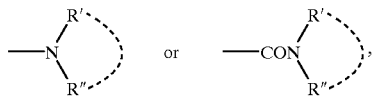

in which R represents a linear or branched alkyl group comprising 1 to 6 carbon atoms and in which R' and R" are identical or different and independently represent a linear or branched alkyl group comprising 1 to 6 carbon atoms, or R' and R", together with the nitrogen atom to which they are bound, represent a 5- or 7-membered ring which can comprise at least one other heteroatom selected from oxygen, sulphur, and nitrogen, said nitrogen being optionally substituted with an R''' group which is a linear or branched alkyl group comprising 1 to 6 carbon atoms, an —$OCOR_6$ or —$COOR_6$ group, wherein $R_6$ represents a straight or branched alkyl group comprising 1 to 6 carbon atoms or a cycloalkyl group comprising 3 to 6 carbon atoms or a phenyl group, optionally substituted with at least one substituent selected from the group consisting of:

a halogen, a linear or branched alkyl group comprising 1 to 12 carbon atoms, a linear or branched alkoxy group comprising 1 to 12 carbon atoms, a haloalkyl or haloalkoxy group corresponding to the ($C_1$–$C_{12}$) alkyl or alkoxy groups above respectively which are substituted with at least one halogen atom, a linear or branched alkenyl group comprising 2 to 12 carbon atoms, an —$NH_2$ group, an —NHR group, R representing a linear or branched alkyl group comprising 1 to 6 carbon atoms, a

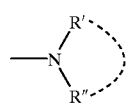

group in which R' and R" are identical or different and independently represent a linear or branched alkyl group comprising 1 to 6 carbon atoms, or R' and R", together with the nitrogen atom to which they are bound, represent a 5- or 7-membered ring which can comprise at least one other heteroatom selected from oxygen, sulphur, and nitrogen, said nitrogen being optionally substituted with an R''' group which is a linear or branched alkyl group comprising 1 to 6 carbon atoms, and a methacryloyl group or an acryloyl group; or at least two of the $R_3$ groups, which are adjacent, form a 5- to 6-membered aromatic or non-aromatic ring which can comprise at least one heteroatom selected from the group consisting of oxygen, sulphur, and nitrogen and/or at least one substituent selected from the group consisting of a $C_1$–$C_6$ alkyl group which is linear or branched, a $C_1$–$C_6$ alkoxy group which is linear or branched, and an amine group of formula —$NH_2$, —NHR, or

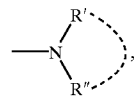

in which R represents a linear or branched alkyl group comprising 1 to 6 carbon atoms and in which R' and R" are identical or different and independently represent a linear or branched alkyl group comprising 1 to 6 carbon atoms, or R' and R", together with the nitrogen atom to which they are bound, represent a 5- or 7-membered ring which can comprise at least one other heteroatom selected from oxygen, sulphur, and nitrogen, said nitrogen being optionally substituted with an R''' group which is a linear or branched alkyl group comprising 1 to 6 carbon atoms;

m is an integer of 0 to 4;

$R_4$, which are identical or different, represent, independently:

a halogen or a $C_1$–$C_6$ alkyl group which is linear or branched; and n is an integer of 0 to 4.

2. A compound according to claim 1, wherein n is 0.

3. A compound according to claim 1, wherein $R_1$ and $R_2$ are identical or different and independently represent optionally substituted aryl or heteroaryl groups, the basic structure of which is selected from the group consisting of phenyl, naphthyl, biphenyl, pyridyl, furyl, benzofuryl, dibenzofuryl, N—($C_1$–$C_6$)alkylcarbazole, thienyl, benzothienyl, dibenzothienyl, and julolidinyl groups; or wherein $R_1$ and $R_2$ together form an adamantyl or norbornyl group.

4. A compound according to claim 1, wherein no adjacent $R_3$ substituents form a ring.

5. A compound according to claim 1, wherein at least two adjacent $R_3$ groups together form a 5- to 6-membered aromatic or non-aromatic ring which can comprise at least one heteroatom selected from the group consisting of oxygen, sulphur, and nitrogen and/or at least one substituent selected from the group consisting of a $C_1$–$C_6$ alkyl group which is linear or branched, a $C_1$–$C_6$ alkoxy group which is linear or branched, and an amine group of formula —$NH_2$, —NHR, or

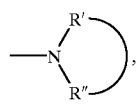

as defined in claim 1 with regard to substituents of the basic structure of the aryl or heteroaryl group representing $R_1$ or $R_2$.

6. A compound according to claim 1 having one of the following formulae (I.1) or (I.2):

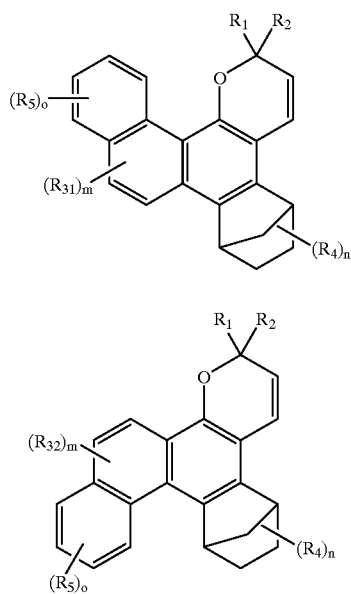

(I.1)

(I.2)

wherein:

$R_5$ represents a $C_1$–$C_6$ alkyl group which is linear or branched, a $C_1$–$C_6$ alkoxy group which is linear or branched, or an amine group of formula —$NH_2$, —NHR, or

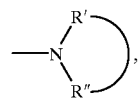

as defined in claim 1 with regard to substituents of the basic structure of the aryl or heteroaryl group representing $R_1$ or $R_2$;

m and o are integers of 0 to 2 and 0 to 4, respectively, $R_1$, $R_2$, $R_4$, and n are as defined in claim 1, and $R_{31}$ and $R_{32}$ represent, independently, a group having the same definition as that given for $R_3$ in claim 1.

7. A compound according to claim 6, wherein n is 0.

8. A method of preparing a compound according to claim 1, said method comprising:

condensing an intermediate of the following formula II.1:

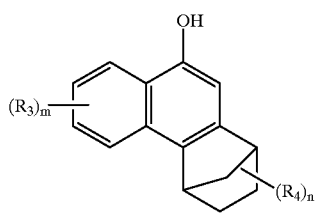

(II.1)

in which $R_3$, $R_4$, m, and n are as defined in claim 1, with at least one derivative of propargylic alcohol having the following formula (III):

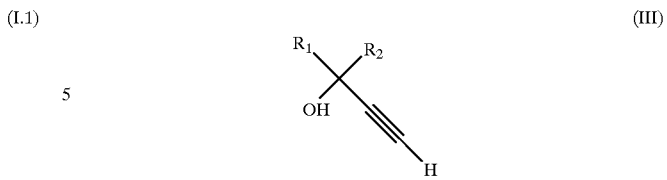

(III)

in which $R_1$ and $R_2$ are as defined in claim 1, said condensing being optionally carried out in the presence of a catalyst; or with at least one aldehyde derivative, having the following formula (III'):

(III')

in which $R_1$ and $R_2$ are as defined in claim 1, said condensing being optionally carried out in the presence of a metallic complex.

9. A method according to claim 8, wherein said condensing is carried out with at least one derivative of propargylic alcohol and wherein said catalyst is selected from the group consisting of para-toluenesulphonic acid, dodecylsulphonic acid, and bromoacetic acid.

10. A method according to claim 8, wherein said condensing is carried out with at least one aldehyde derivative and wherein said metallic complex is a titanium complex.

11. A method according to claim 8, wherein the compound has the following formula I.1:

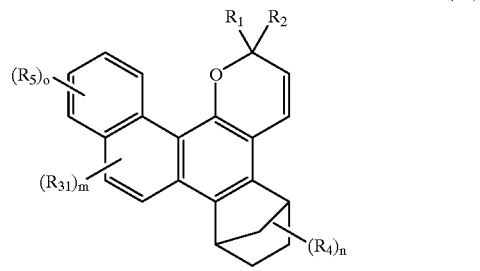

(I.1)

wherein the intermediate has the following formula II.2:

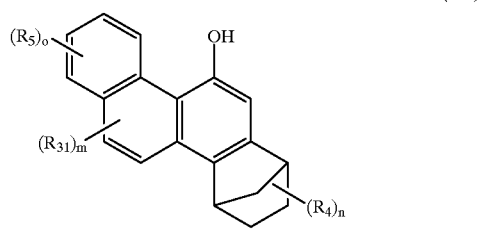

(II.2)

and wherein $R_5$ represents a $C_1$–$C_6$ alkyl group which is linear or branched, a $C_1$–$C_6$ alkoxy group which is linear or branched, or an amine group of formula —$NH_2$— NHR, or ,

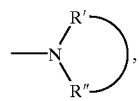

as defined in claim 1 with regard to substituents of the basic structure of the aryl or heteroaryl group representing $R_1$ or $R_2$;

o is an integer of 0 to 4; and $R_{31}$ represents a group having the same definition as that given for $R_3$ in claim 1.

12. A method according to claim 8, wherein the compound has the following formula I.2:

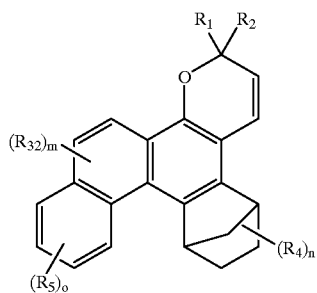

(I.2)

wherein the intermediate has the following formula II.3:

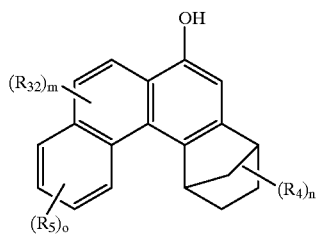

(II.3)

and wherein $R_5$ represents a $C_1$–$C_6$ alkyl group which is linear or branched, a $C_1$–$C_6$ alkoxy group which is linear or branched, or an amine group of formula —$NH_2$, —NHR, or

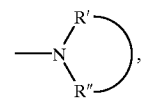

as defined in claim 1 with regard to substituents of the basic structure of the aryl or heteroaryl group representing $R_1$ or $R_2$;

o is an integer of 0 to 4; and $R_{32}$ represents a group having the same definition as that given for $R_3$ in claim 1.

13. A (co)polymer and/or reticulate obtained by polymerising and/or cross-linking at least one monomer comprising a compound according to claim 1.

14. A photochromic compound, characterised in that it is constituted by a compound according to claim 1, or by a mixture of at least two compounds according to claim 1, or by a mixture of at least one compound according to claim 1 with at least one other photochromic compound of another type and/or at least one non-photochromic colouring agent.

15. A photochromic composition, characterised in that it comprises:

at least one compound according to claim 1, and/or at least one linear or cross-linked (co)polymer which contains, in its structure, at least one compound according to claim 1, and optionally, at least one other photochromic compound of another type and/or at least one non-photochromic colouring agent and/or at least one stabilising agent.

16. A (co)polymer matrix, characterised in that it comprises:

at least one compound according to claim 1.

17. A matrix according to claim 16, characterised in that the (co)polymer is selected from:

alkyl, cycloalkyl, (poly or oligo)ethylene glycol, aryl or arylalkyl mono-, di-, tri-, or tetraacrylate or mono-, di-, tri-, or tetramethacrylate which is optionally halogenated or which comprises at least one ether and/or ester and/or carbonate and/or carbamate and/or thiocarbamate and/or urea and/or amide group;

polystyrene, polyether, polyester, polycarbonate, polycarbamate, polyepoxy, polyurea, polyurethane, polythiourethane, polysiloxane, polyacrylonitrile, polyamide, aliphatic or aromatic polyester, vinylic polymers, cellulose acetate, cellulose triacetate, cellulose acetate-propionate, or polyvinylbutyral;

difunctional monomers having the formula below:

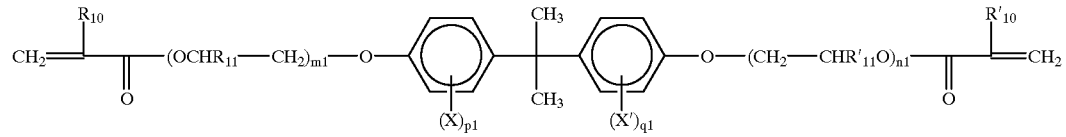

in which:
$R_{10}$, $R'_{10}$, $R_{11}$, and $R'_{11}$ are identical or different and represent independently a hydrogen or a methyl group;
$m_1$ and $n_1$ are, independently, integers between 0 and 4 inclusive;
X and X', which are identical or different, are halogens;
$p_1$ and $q_1$ are, independently, integers between 0 and 4 inclusive;
a copolymer of at least two types of copolymerisable monomers selected from the precursor monomers of the polymers listed above; and
combinations thereof.

18. An ophthalmic or solar article comprising:
at least one matrix according to claim 16.

19. An article according to claim 18, characterised in that it is constituted by a lens, by a glazing, or by an optical device.

20. An ophthalmic or solar article comprising:
at least one compound according to claim 1.

21. An article according to claim 20, characterised in that it is constituted by a lens, by a glazing, or by an optical device.

22. A (co)polymer matrix, characterised in that it comprises:
at least one co(polymer) and/or reticulate according to claim 13.

23. A matrix according to claim 22, characterised in that the (co)polymer is selected from:
alkyl, cycloalkyl, (poly or oligo)ethylene glycol, aryl or arylalkyl mono-, di-, tri-, or tetraacrylate or mono-, di-, tri-, or tetramethacrylate which is optionally halogenated or which comprises at least one ether and/or ester and/or carbonate and/or carbamate and/or thiocarbamate and/or urea and/or amide group;
polystyrene, polyether, polyester, polycarbonate, polycarbamate, polyepoxy, polyurea, polyurethane, polythiourethane, polysiloxane, polyacrylonitrile, polyamide, aliphatic or aromatic polyester, vinylic polymers, cellulose acetate, cellulose triacetate, cellulose acetate-propionate, or polyvinylbutyral;
difunctional monomers having the formula below:

$R_{10}$, $R'_{10}$, $R_{11}$, and $R'_{11}$ are identical or different and represent independently a hydrogen or a methyl group;
$m_1$ and $n_1$ are, independently, integers between 0 and 4 inclusive;
X and X', which are identical or different, are halogens;
$p_1$ and $q_1$ are, independently, integers between 0 and 4 inclusive;
a copolymer of at least two types of copolymerisable monomers selected from the precursor monomers of the polymers listed above; and
combinations thereof.

24. An ophthalmic or solar article comprising:
at least one matrix according to claim 22.

25. An article according to claim 24, characterised in that it is constituted by a lens, by a glazing, or by an optical device.

26. An ophthalmic or solar article comprising:
at least one (co)polymer and/or reticulate according to claim 13.

27. An article according to claim 26, characterised in that it is constituted by a lens, by a glazing, or by an optical device.

28. A (co)polymer matrix, characterised in that it comprises:
at least one composition according to claim 15.

29. A matrix according to claim 28, characterised in that the (co)polymer is selected from:
alkyl, cycloalkyl, (poly or oligo)ethylene glycol, aryl or arylalkyl mono-, di-, tri-, or tetraacrylate or mono-, di-, tri-, or tetramethacrylate which is optionally halogenated or which comprises at least one ether and/or ester and/or carbonate and/or carbamate and/or thiocarbamate and/or urea and/or amide group;
polystyrene, polyether, polyester, polycarbonate, polycarbamate, polyepoxy, polyurea, polyurethane, polythiourethane, polysiloxane, polyacrylonitrile, polyamide, aliphatic or aromatic polyester, vinylic polymers, cellulose acetate, cellulose triacetate, cellulose acetate-propionate, or polyvinylbutyral;
difunctional monomers having the formula below:

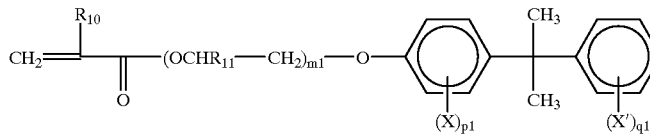

in which:

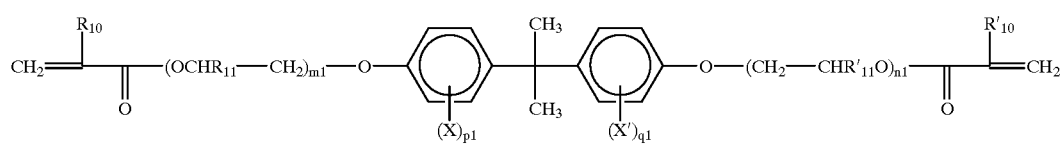

in which:

$R_{10}$, $R'_{10}$, $R_{11}$, and $R'_{11}$ are identical or different and represent independently a hydrogen or a methyl group;

$m_1$ and $n_1$ are, independently, integers between 0 and 4 inclusive;

X and X', which are identical or different, are halogens;

$p_1$ and $q_1$ are, independently, integers between 0 and 4 inclusive;

a copolymer of at least two types of copolymerisable monomers selected from the precursor monomers of the polymers listed above; and combinations thereof.

30. An ophthalmic or solar article comprising:

at least one matrix according to claim 28.

31. An article according to claim 30, characterised in that it is constituted by a lens, by a glazing, or by an optical device.

32. An ophthalmic or solar article comprising:

at least one composition according to claim 15.

33. An article according to claim 32, characterised in that it is constituted by a lens, by a glazing, or by an optical device.

* * * * *